US011172841B2

(12) United States Patent
Pokorney

(10) Patent No.: US 11,172,841 B2
(45) Date of Patent: Nov. 16, 2021

(54) ELECTRODE CATHETER ASSEMBLY AND METHOD FOR THE MANUFACTURE THEREOF

(71) Applicant: Alandra Medical SAPI de CV, Mexico City (MX)

(72) Inventor: James L. Pokorney, Northfield, MN (US)

(73) Assignee: Alandra Medical SAPI de CV, Mexico City (MX)

( * ) Notice: Subject to any disclaimer, the term of this patent is extended or adjusted under 35 U.S.C. 154(b) by 356 days.

(21) Appl. No.: 16/010,875

(22) Filed: Jun. 18, 2018

(65) Prior Publication Data

US 2018/0368728 A1 Dec. 27, 2018

Related U.S. Application Data

(60) Provisional application No. 62/522,804, filed on Jun. 21, 2017.

(51) Int. Cl.
*A61B 5/0538* (2021.01)
*A61B 5/00* (2006.01)
(Continued)

(52) U.S. Cl.
CPC .......... *A61B 5/0538* (2013.01); *A61B 5/6852* (2013.01); *B29C 45/14065* (2013.01);
(Continued)

(58) Field of Classification Search
None
See application file for complete search history.

(56) References Cited

U.S. PATENT DOCUMENTS

| 5,524,337 A | 6/1996 | Houser et al. |
| 5,855,552 A | 1/1999 | Houser et al. |
(Continued)

FOREIGN PATENT DOCUMENTS

| DE | 102005001225 B4 * | 10/2012 | ............ B23P 19/084 |
| EP | 0771251 A1 * | 5/1997 | ............ B25B 27/205 |
| WO | 2008/060142 A1 | 5/2008 | |

OTHER PUBLICATIONS

Bow Opening Pliers, Amazon.com, https://www.amazon.com/Opening-Pliers-Reverse-Action-Pendant/dp/B01C3BWOPC/, Feb. 22, 2016 Accessed Aug. 10, 2020. (Year: 2016).*
(Continued)

*Primary Examiner* — Peter L Vajda
*Assistant Examiner* — Adrianna N Konves
(74) *Attorney, Agent, or Firm* — Collard & Roe, P.C.

(57) ABSTRACT

An alignment tool to be used in a method for the manufacture of an electrode catheter assembly includes an alignment handle, a grooved longitudinal axis which is opposed to the alignment handle and which includes a channel or groove in the radial direction, wherein the grooved longitudinal axis has alignment grooves and alignment surfaces to precisely allow alignment and separation of electrode rings; two arms or tines formed by the channel or groove, wherein the arms or tines are compressible in radial direction to the grooved longitudinal axis; a removable proximal shoulder ring, wherein the proximal shoulder ring has a shoulder surface and an internal opening, wherein the internal opening allows the shoulder proximal ring to slide on or off the grooved longitudinal axis, a control surface, and a distal shoulder surface.

15 Claims, 10 Drawing Sheets

(51) Int. Cl.
*B29C 45/14* (2006.01)
*B29K 75/00* (2006.01)
*B29L 31/00* (2006.01)
*A61M 25/00* (2006.01)
*A61M 25/02* (2006.01)

(52) U.S. Cl.
CPC .. *B29C 45/14467* (2013.01); *B29C 45/14549* (2013.01); *A61B 2562/0209* (2013.01); *A61B 2562/043* (2013.01); *A61B 2562/125* (2013.01); *A61B 2562/227* (2013.01); *A61M 25/0009* (2013.01); *A61M 2025/0206* (2013.01); *B29K 2075/00* (2013.01); *B29L 2031/7542* (2013.01)

(56) References Cited

U.S. PATENT DOCUMENTS

| | | |
|---|---|---|
| 5,951,929 A | 9/1999 | Wilson |
| 6,757,970 B1 | 7/2004 | Kuzma et al. |
| 9,326,729 B2 | 5/2016 | Mori |

OTHER PUBLICATIONS

Anter et al., High-Resolution Mapping of Scar-Related Atrial Arrhythmias Using Smaller Electrodes With Closer Interelectrode Spacing; Circulation: Arrhythmia and Electrophysiology, American Heart Association; Jun. 1, 2015, Accessed Aug. 10, 2020 (Year: 2015).*
Machine English Translation of DE102005001225B4, Oct. 25, 2012, Accessed Aug. 10, 2020 (Year: 2012).*

* cited by examiner

ELECTRODE CATHETER ASSEMBLY AND METHOD FOR THE MANUFACTURE THEREOF

CROSS REFERENCE TO RELATED APPLICATIONS

This application claims priority under 35 U.S.C. § 119 (e) from and the benefit of U.S. Provisional Patent Application Ser. No. 62/522,804, filed on Jun. 21, 2017, the disclosure of which is incorporated by reference.

FIELD OF THE INVENTION

The present invention mainly refers to an improved electrode catheter assembly, a related method used in the manufacturing thereof, and an alignment tool to help in the manufacture of the mentioned electrode catheter assembly.

BACKGROUND OF THE INVENTION

In many areas of the body, including the stomach lining, conductivity can be measured using a series of metal, or electrodes, attached to a polymer catheter. Each electrode is connected within the catheter to a conducting wire that is connected to a controlling and measuring instrument located outside the body.

In most instances, the quality of the electrode design is an important predictor of the overall quality of the measurement of interest. In particular, the way of how the metal electrodes are interfaced with the polymer catheter is an important design consideration. In many designs, the electrodes need to be precisely spaced apart from one another by a known distance. In other designs, the electrode surface needs to be fully flush with the surrounding catheter surfaces to minimize tissue trauma and to support good contact with the adjacent, abutting tissue. Also, to be economically viable, a simple assembly process that results in a highly repeatable electrode catheter product is an important design requirement, especially if the components used are not, or cannot, be manufactured with dimensions that are accurate, precise and repeatable.

The manufacturing of the catheter assemblies involves several techniques in which the electrode rings are arranged in such a way that they present a distance therebetween, but none of these known techniques assure that each electrode ring be arranged apart from other at the required distance to not interfere with the polymer catheter.

Document WO 2008/060142 describes a method for making a catheter, comprising an electrode housing which comprises a prismatic part in the surface of which a number of grooves is formed, providing at least one electrode, connecting an electrical conductor to each electrode, wherein the electrical conductor extends in axial direction relative to the electrode, sliding each electrode onto the electrode housing, wherein the electrical conductor thereof slides through one of the grooves of the housing, positioning the electrode on the electrode housing, arranging the electrode housing with the electrode thereon in a mould cavity of a mould, and arranging round the electrode housing a layer of plastic with an outer diameter substantially the same as that of the electrode U.S. Pat. No. 6,757,970 B1 describes a multicontact electrode array suitable for implantation in living tissue, which includes a distal end having multiple spaced-apart ring contacts or a pattern of spaced-apart electrode contacts carried on a flexible carrier. Each electrode contact is resistance welded to a respective wire that is wound helically inside a silicon tube. The center of the helix defines a lumen wherein a positioning stylet, or other suitable positioning tool, may be removably inserted when the electrode array is implanted. The electrode array is made using a method that includes, as an initial step, winding lead wires around a suitable mandrel forming a helix configuration. Next, a non-conductive silicone tube jacket is placed around the wound wires, exposing the distal lead ends of the wires at a distal end of the tube. A welding process is then used to bond each wire tip to a corresponding metal electrode contact which has been preassembled by resistance welding to a metal foil structural carrier. The electrode array, including the metal foil structural carrier, is then formed into a tube by drawing it through a die. The excess foil material at the distal tip is then trimmed and a heat-shrinkable tube is placed around the assembled foil tube to prevent leakage of the polymer filler material through the joining longitudinal line of the carrier. Next, the foil tube is injected with a polymer filler material to void any gaps between the lead wires and contacts. To avoid filling the central lumen with the polymer filler material, a central core or stylet is temporarily placed inside the lumen. The heat-shrinkable tube is then mechanically removed. The fabrication method is finalized by inserting the preassembled electrode array into a hot acid mixture, which etches away the metal foil carrier, exposing the contacts at the surface of a distal end of the electrode array U.S. Pat. No. 5,855,552 B1 and U.S. Pat. No. 5,524,337 B1 describe a catheter having an elongated polymeric body with hollow encircling ring electrodes thereon, and a method of forming the same. Ring electrodes are each connected to an external electrical circuit by wires extending through the lumen, the wires each passing through an aperture through a wall of the body and being connected to an interior surface of the ring electrode. The tubular body of the catheter is expanded into a tight interference fit with the interior surfaces of the ring electrodes by heating the body to a temperature approaching its glass transition temperature to permit relief of internal stresses.

U.S. Pat. No. 5,951,929 B1 describes a method of forming a catheter having an inner layer, an intermediate braided layer and an outer jacket, wherein the intermediate braided layer terminates axially before the inner layer, leaving a forward end portion of the inner layer exposed, the method comprising the steps of: a) before applying the outer jacket, loading a plastic sleeve over a forward end of the intermediate braided layer adjacent the forward end portion of the inner layer; b) heating the plastic sleeve to a temperature sufficient to melt the plastic sleeve; c) loading a terminal tip having an axial length over a forward end portion of the inner layer into abutting relationship with the forward end of the intermediate braided layer such that the terminal tip is supported by the forward end portion of the inner layer along all of the axial length of the terminal tip and not reinforced anywhere along the axial length by the intermediate braided layer; d) loading the outer jacket over the braided layer; e) loading a shrinkable tube over the outer jacket; and f) heating to cause the shrinkable tube to compress the outer jacket into the interstices of the intermediate braided layer.

U.S. Pat. No. 9,326,729 B1 describes an electrode catheter provided with a catheter shaft, an operating handle provided with a connector, a tip electrode, ring-shaped electrodes, lead wires connected to the tip electrode and the ring-shaped electrodes, respectively, and a pull wire fixed to the tip electrode. The catheter shaft is constituted of a shaft proximal end portion formed of a metal tube having a spiral slit formed in a tip portion, a shaft distal end portion formed of a resin tube of multi-lumen structure, and a resin covering layer covering outer peripheries of the shaft proximal end portion and a rear end portion of the shaft distal end portion. The lead wires and the pull wire extend through different lumens of the resin tube constituting the shaft distal end portion. This electrode catheter can exhibit good kink resistance, torque transmissibility and pushability in the entire shaft.

It is well known in the state of the art that insert molding using insert mold tooling require component parts that are of a precise and repeatable dimension, otherwise the molding process can either cause damage to the parts or contribute to significant quality issues. Polymer tubing used in electrode catheters is typically not precise nor repeatable in diameter due to variations in the extrusion fabrication process. Therefore, an insert molding process is not a preferred assembly method.

SUMMARY OF THE INVENTION

One aspect of the invention is to provide an alignment tool to be used in a method for the manufacture of an electrode catheter assembly to align electrode rings to a specific distance, the alignment tool comprising an alignment handle, a grooved longitudinal axis opposed to the alignment handle, wherein the grooved longitudinal axis comprises a channel or groove in the radial direction to conform two compressible arms or tines and which allows the compression of said compressible arms or tines to a diameter smaller than the inner diameter of the electrode rings to remove the alignment tool once the electrode rings have been placed in the desired position. Additionally, the grooved longitudinal axis has alignment grooves and alignment surfaces to precisely allow alignment and separation of the electrode rings. Likewise, the alignment tool comprises a removable proximal shoulder ring, a control surface, and a distal shoulder surface; wherein said proximal shoulder ring has a shoulder surface and an internal opening, and wherein the internal opening allows that the shoulder proximal ring be slid on or off the grooved longitudinal axis. The alignment handle of the alignment tool is made of an elastic material, such as plastic or stainless steel or aluminum.

In other aspect, the present invention refers to a method for manufacturing an electrode catheter assembly, comprising the steps of: selecting an alignment tool, placing and aligning a series of electrode rings on the grooved longitudinal axis of the alignment tool by applying forces on arms or tines of the alignment tool. Then, placing a proximal shoulder ring in opposite direction to a distal shoulder surface of the alignment tool, wherein the proximal shoulder ring has a shoulder surface and an internal opening to allow that conducting wires pass therethrough. Then, sliding a heat shrinkable tube on the outer surface of the electrode rings, distal shoulder surface and shoulder surface by releasing the arms or tines from the forces. Then, applying a first heat treatment to the heat shrinkable tube to partially reduce its diameter and adjust it to the outer surface of the electrode rings, the distal shoulder surface and the shoulder surface. The proximal shoulder ring engages on the alignment tool to an alignment handle of the alignment tool, and the shoulder distal element is placed opposite to the proximal shoulder ring forming a structure in the form of an "hour glass" or "dog bone". Then, removing the proximal shoulder ring and the alignment tool by applying forces to the arms or tines. Inserting a proximal catheter tube into the proximal end of the heat shrinkable tube, and a distal catheter tube into the distal end of the heat shrinkable tube. After, applying a second heat treatment, different to the first heat treatment, to the heat shrinkable tube to reduce its diameter and contact the outer surface of the proximal catheter tube and the outer surface of the distal catheter tube. Then, injecting sufficient polymer material through the inner space of the heat shrinkable tube for contacting the inner surfaces of the electrode rings, the side surface of the proximal catheter tube, the side surface of the distal catheter tube, hardening the polymer material, and finally removing the heat shrinkable tube, wherein said heat shrinkable tube is removed by cutting it or tearing it. The alignment tool, the proximal shoulder ring, the distal shoulder element and the heat shrinkable tube are removed without altering the alignment of electrode rings once the injected polymer material has hardened, leaving the outer surface of the electrode rings free of polymer material.

The precise spacing between the electrode ring is an important parameter for the design of an electrode catheter every time that by applying an electrical signal to the electrodes what is sought is that there is no interference therebetween due to a non-appropriate distance. The present invention also provides an electrode catheter having a series of metal electrode rings embedded into a shrinkable polymeric tube without the need for expensive and dimensionally inappropriate molding processes for the manufacturing of such system. Particularly, the present invention refers to an alignment tool, a method for manufacturing an electrode catheter assembly, and an improved electrode assembly.

The present invention solves the technical problem of providing an electrode system without using expensive molding techniques that do not ensure an outer surface of electrode rings smooth and free of polymer. The method of the present invention ensures a smooth surface between the proximal and distal catheters and integrated electrodes, and between adjacent electrodes, though the diameter of the catheter shaft is not always consistent, precise or accurate.

The present invention also solves the technical problem of specifically aligning and separating each electrode ring to a distance necessary to not interfere with the polymer catheter.

Therefore, the main object of the present invention is to provide an improved method for manufacturing an electrode catheter assembly. Another object of the present invention is to provide an alignment tool for the manufacture of an electrode catheter assembly that solves the deficiencies of the prior art.

These and other objectives and advantages are obtained by applying the method of the present invention and by using the appropriate alignment tool, in their different embodiments.

DETAILED DESCRIPTION OF THE PREFERRED EMBODIMENTS

Figure 1:
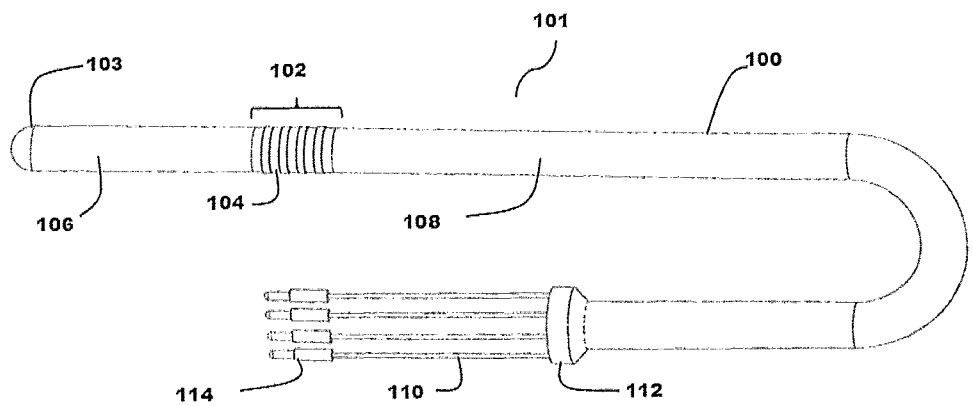
FIG. 1 is a schematic view of an electrode catheter assembly.

FIG. 1, shows an electrode catheter (100) including an electrode catheter assembly (101) which is the basis of this invention. It is to be noticed that the present invention focuses more on the electrode catheter assembly (101), and less in all the electrode catheter designs or methods to manufacturing said electrode catheter (100). The electrode catheter system includes catheter tips (103), a hub (112), connectors (114) and the manufacture thereof.

The present specification is related to an electrode catheter assembly (101) comprising one or more electrode rings (102) embedded in an adhesive (104) bonded to a distal tube (106) and a proximal tube (108). A conducting wire (110) is connected to each electrode ring (102) and is located within the distal tube (108) and extending into and beyond the hub (112). Each conducting wire (110) in the electrode catheter assembly (101) is later terminated in a connector (114) included in the electrode catheter (100). In use, an electrical current can be transmitted between the electrode ring (102) and an associated connector (114).

Figure 2A:
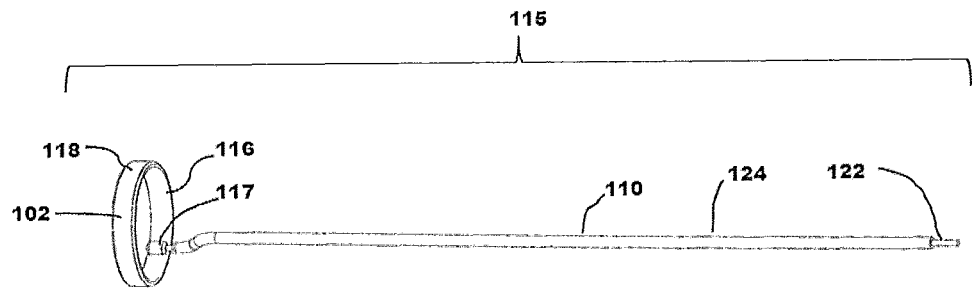
FIG. 2A depicts a preferred embodiment of an electrode ring assembly.

FIG. 2A, shows a preferred embodiment of an electrode ring assembly (115). In this embodiment, the electrode ring assembly (115) includes the electrode ring (102), the conducting wire (110), and a conductive bonding material (117). The electrode ring (102) has an inner surface (116) and an outer surface (118). The electrode ring (102) is composed of a conductive material such as silver or platinum or gold or stainless steel, or some other biocompatible, low electrical impedance material. The electrode ring (102) is shown with a rectangular cross section. However, there are several embodiments in which the electrode ring (102) can be configured, such as, but not limited to, a round or oval or triangular form, each having an inner surface and an outer surface. The electrode ring (102) is connected to the conducting wire (110) by direct welding, brazing, or soldering using the conductive bonding material (117). The conductive bonding material (117) can be selected from one of silver, a silver alloy, a lead alloy, a conductive polymer or any other material that can reliable connect the two components while allowing a low impedance electrical pathway. The conducting wire (110) is composed of a conductor (122) surrounded by a jacket or an insulator (124). The conductor (122) is selected from one of silver, copper, gold or other low electrical impedance material, and the isolator (124) is selected of a high impedance material such as Teflon, Nylon or another suitable high impedance polymer material.

Figure 2B:
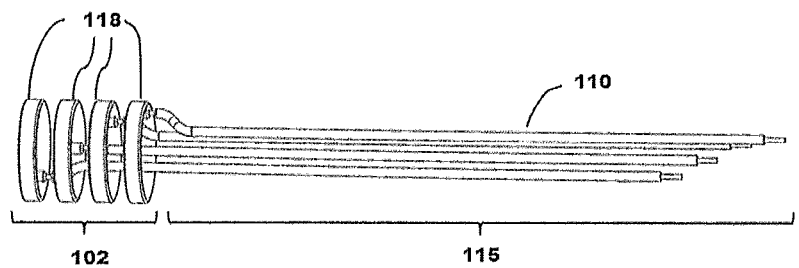
FIG. 2B depicts a series of four electrode ring assemblies.

Referring to FIG. 2B, it shows a series of four electrode ring assemblies (115) shown axially aligned and spaced a distance apart. In the embodiment of the FIG. 2B, the conducting wire (110) is oriented in a similar direction for all the assemblies (115), which is a typical arrangement in an electrode catheter design. It is the object of this invention to package a series of electrodes as shown in FIG. 2B on an electrode catheter (100) in such a way that only the outer surfaces (118) of the electrode rings (102) are exposed to tissue or body fluid, and that the electrical pathways for each electrode ring assembly (115) are completely isolated from other electrode ring assemblies (115). In other embodiments of the invention, it should be noted that the number of electrode ring assemblies (115) can vary from one to as many as twenty or so depending on the application of the catheter assembly (101). It should be noted that the outside diameter of each electrode ring (102) could vary due to variations in the manufacturing process of the same. In accordance with the method of the present invention, the manufacture of the electrode catheter assembly (101) is not affected by variations in the electrode diameter.

Figure 3A:
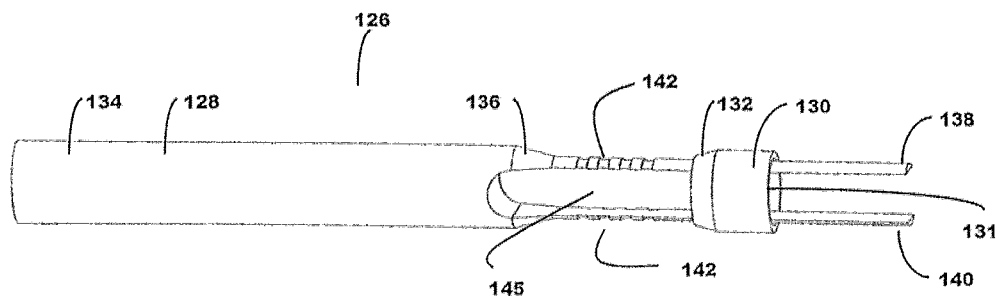
FIG. 3A is a schematic view of an alignment tool.
Figure 3B:
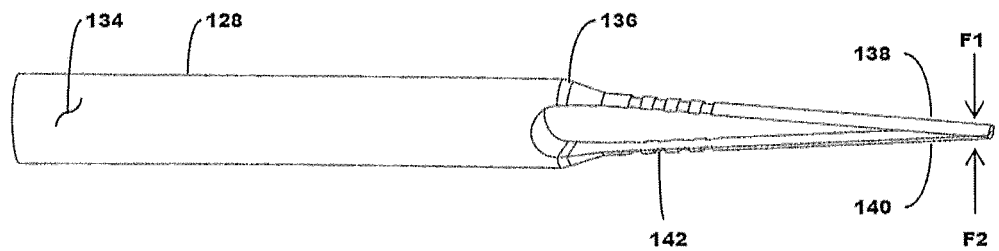
FIG. 3B is another schematic view of an alignment tool.

FIG. 3A is an embodiment of an alignment tool (126) comprising an alignment handle (128) and a removable proximal shoulder ring (130) having a shoulder surface (132). The proximal shoulder ring (130) has an internal opening (131) that allows the proximal shoulder ring (130) to slide on or off the alignment handle (128). The alignment tool (126) has a control surface (134), a distal shoulder surface (136), a first arm or tine (138), a second arm or tine (140), wherein said arms or tines (138, 140) are configured through a channel or groove (145) formed in longitudinal direction and opposite to the alignment handle (128), such arms or tines (138, 140) comprise alignment grooves (142) on which are arranged and positioned the electrode rings (102). The arms or tines (138, 140) are easily compressible in axial direction (see FIG. 3B) along the alignment tool (126) to allow the insertion of the electrode rings (102) and the release of said arms or tines (138, 140) once the electrode rings (102) have been positioned, spaced and adjusted in a shrinkable polymer tube (see FIG. 3G). The alignment grooves (142) are designed to accept the inner surface of the electrode rings (102). In the embodiment shown in FIG. 3A, but without limiting the scope of the present invention, the alignment handle (128) has four sets of alignment grooves (142) to accommodate up to four electrode rings (102). Other embodiments of the alignment tool (126) could allow for substantially more alignment grooves (142) to consequently allow for more electrode rings (102) to be aligned. The alignment handle (128) is made of an elastic material such as stainless steel or aluminum. When subjected to forces F1 and F2 (see FIG. 3B) applied substantially normal to their outer surfaces, the first arm or tine (138) and the second arm or tine (140) elastically move toward each other. When such forces F1 and F2 are removed, the first arm or tine (138) and second arm or tine (140) go substantially back to their initial position as shown in FIG. 3A.

Figure 3C:
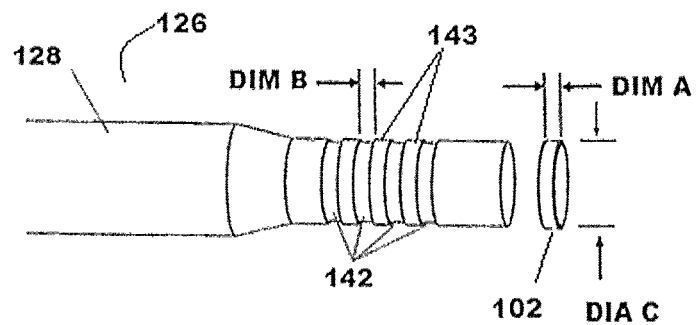
FIG. 3C is a schematic view of a grooved longitudinal axis of the alignment tool.
Figure 3D:
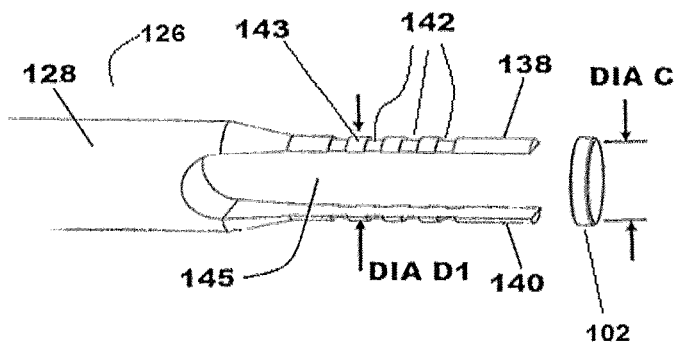
FIG. 3D is a schematic view of the grooved longitudinal axis of the alignment tool with arms or tines.
Figure 3E:
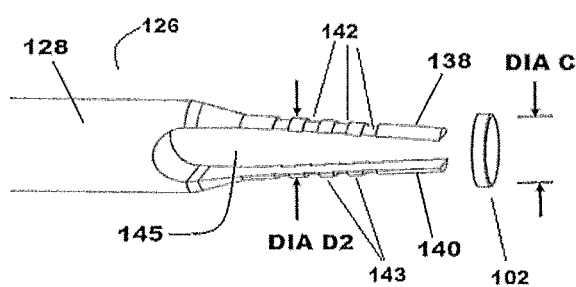
FIG. 3E is a schematic view of the grooved longitudinal axis of the alignment tool with the arms or tines pressed and an embodiment of an electrode ring.
Figure 3F:
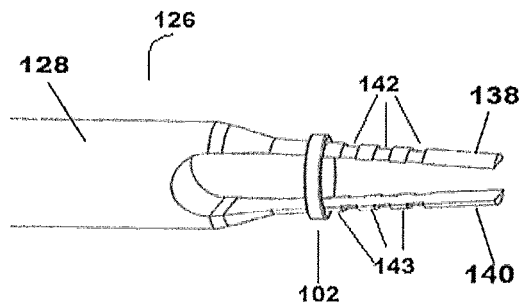
FIGS. 3F to 3H is a schematic view of the grooved longitudinal axis of the alignment tool with the arms or tines.
Figure 3G:
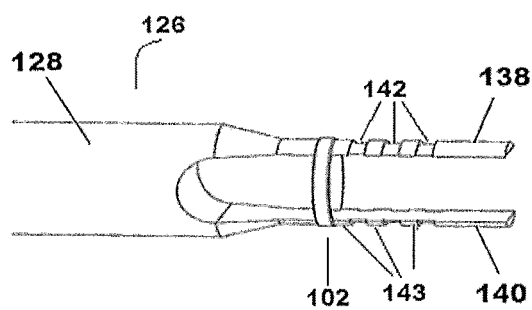
Figure 3H:
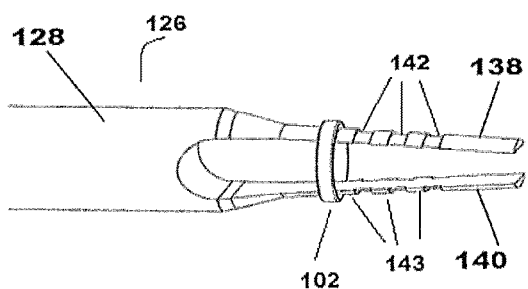

The embodiment of FIGS. 3C and 3D shows an alignment tool (126) which comprises alignment grooves (142) carried out by means of a lathe, and alignment surfaces (143) on a metal or plastic shaft. The arms or tine (138, 140) are created using a finishing milling machine or the like, removing from the opposite end on the longitudinal axis of the alignment handle (128) enough material to form a channel or groove (145) to provide the flexibility of arms or tine (138, 140), for the release of electrode rings (102). To comply with the separation and alignment of the electrode rings (102) certain relationships of dimensions must be complied with. These relationships of dimensions are independent from the number of alignment grooves (142), i.e. they are independent of the specific number of electrode rings (102) which will be aligned on the arms or tines (138, 140). Relations that must be complied with are:

DIM A<DIA C
DIA C<DIA D1 (before compressing the arms or tines (138, 140))
DIA D2 (see FIG. 3E) (after compressing arms or tines (138, 140))<DIA C;
where:
Dimension A (DIM A) is the width of the electrode ring (102);
Dimension B (DIM B) is the width of the alignment groove (142) of the tool;
Diameter C (DIA C) is the inner diameter of the electrode ring (102);
Diameter D1 (DIA D1) is the minimum diameter of the alignment surfaces (143), in original position;
Diameter D2 (DIA D2) is the maximum diameter of the alignment surfaces (143), in the compressed position.

Figure 14:
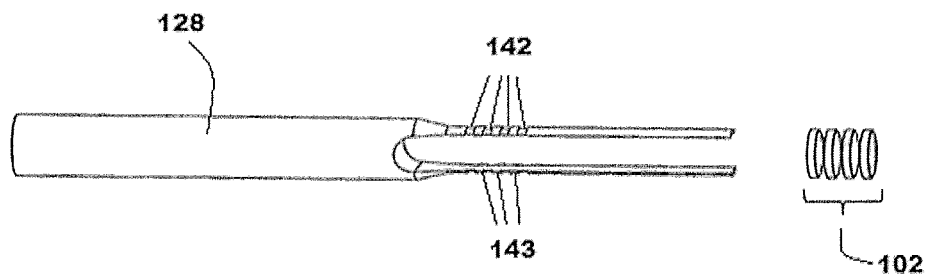
FIG. 14 is another schematic view of the alignment tool and the released electrode rings.

Additionally, the width of the channel or groove (145) in relation to the diameter of the alignment grooves (142) of the alignment tool (126) determines the elastic coefficient of the same alignment tool (126). Moreover, in the embodiment of the alignment tool (126) shown in FIG. 14 the portion opposite to the alignment handle (128) is provided with a large enough length to allow the formation of additional alignment grooves (142) and alignment surfaces (143) as needed.

Additionally, it is required that alignment grooves (142) provide consistent and accurate alignment of the electrode rings (102) with sub-millimeter tolerances, and a separation so that the distance between each alignment groove (142) is 1 mm or thereabouts with a tolerance of tenths of mm or thereabouts.

The advantage associated with the alignment tool (126) of the present invention is that it allows obtaining a precise distancing and alignment of the electrode ring (102) each time. The manufacturing of an electrode catheter system as described in the present invention is easy, economical and quick, and training requirements are minimal for its production or use. It also eliminates the need of expensive tools for the elaboration of a catheter system in which consistent and accurate alignment of the electrode rings (102) is required. Additionally, the alignment tool (126) can be used a several number of times without the need of being recalibrated.

Figure 4:
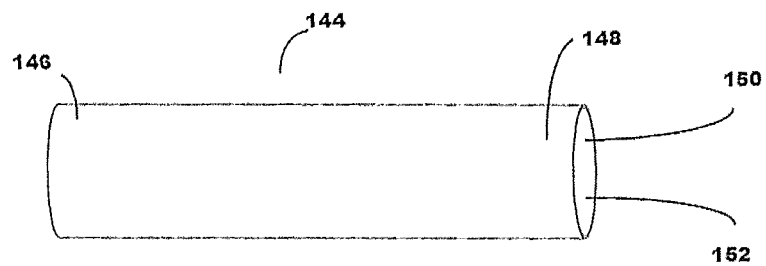
FIG. 4 is a schematic view of a typical embodiment of a shrinkable tube.

The shrinkable tube (144) shown in FIG. 4 represents a typical embodiment of a shrinkable tube (144) used in the assembly method. The shrinkable tube (144) has a distal end (146), a proximal end (148), an inner surface (150), and an interior space (152). The shrinkable tube (144) is composed of a polymer material such as a polyolefin, polyvinyl chloride, Teflon, PET, or another heat shrinkable material. In manufacturing methods using light sensitive liquid fillers, it is advantageous that the shrinkable tube (144) be clear, transparent, or semi-transparent to allow for light transmission.

Figure 5:
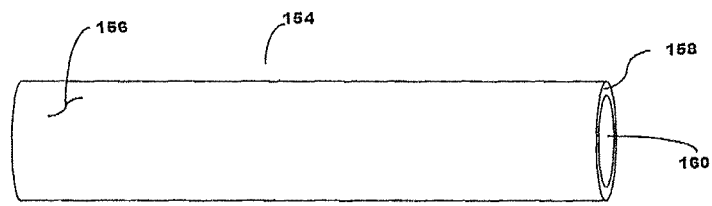
FIG. 5 is a schematic view of a typical embodiment of a proximal catheter tube.

A proximal catheter tube (154) shown in FIG. 5 has an outer surface (156), a side surface (158), and an internal lumen (160). The proximal catheter tube (154) can be made of a biocompatible material such as polyurethane, silicone, PEBAX®, nylon, polyvinyl chloride, polyimide, or another polymeric material. In one preferred embodiment, the proximal catheter tube (154) is made of polyurethane and has two internal lumens (160) and is about one hundred centimeters long.

Figure 6:
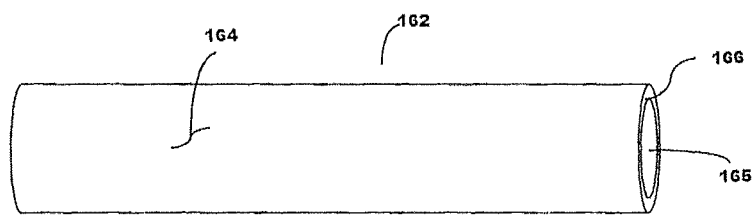
FIG. 6 is a schematic view of a typical embodiment of a distal catheter tube.

A distal catheter tube (162) shown in FIG. 6 has an outer surface (164), an internal lumen (165), and a side surface (166). The distal catheter tube (162) can be made of a biocompatible material such as polyurethane, silicone, PEBAX®, nylon, polyvinyl chloride, polyimide, or another polymer material. In one preferred embodiment, the distal catheter tube (162) is made of polyurethane and has one internal lumen (165), a rounded tip on one end (not shown) and is about 5 centimeters long. It should be noted that the outside diameter of each catheter tube may vary due to variations in the manufacturing process of the same.

Figure 7A:
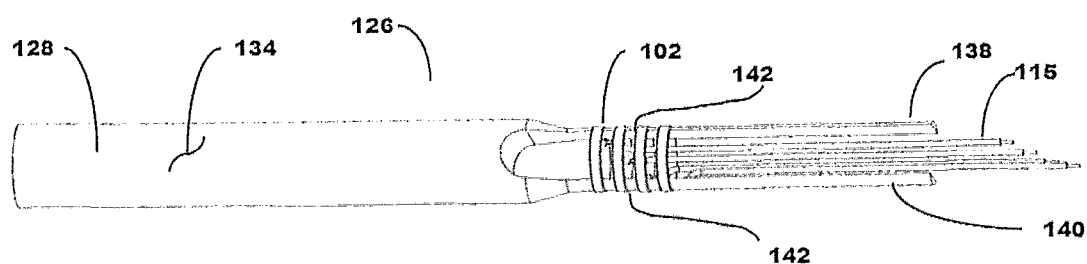
FIG. 7A is a schematic view of electrode ring assemblies mounted in an alignment tool.
Figure 7B:
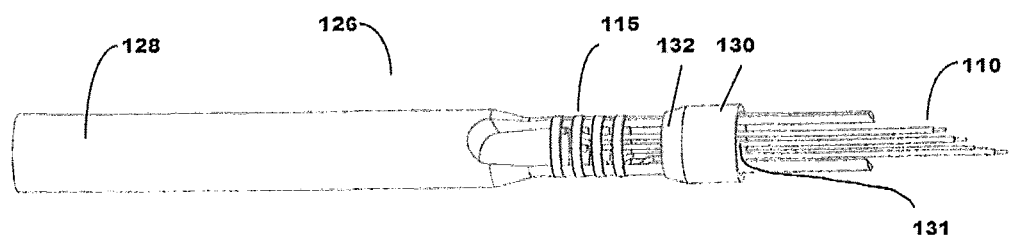
FIG. 7B is a schematic view of electrode ring assemblies and a shoulder ring mounted in an alignment tool.
Figure 8A:
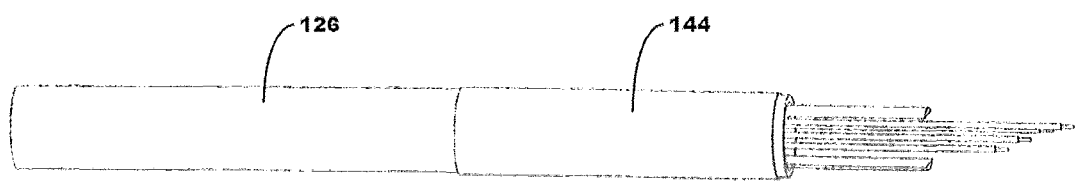
FIG. 8A is a schematic view of the shrinkable tube placed over the components and the alignment tool shown in FIG. 7B.
Figure 8B:
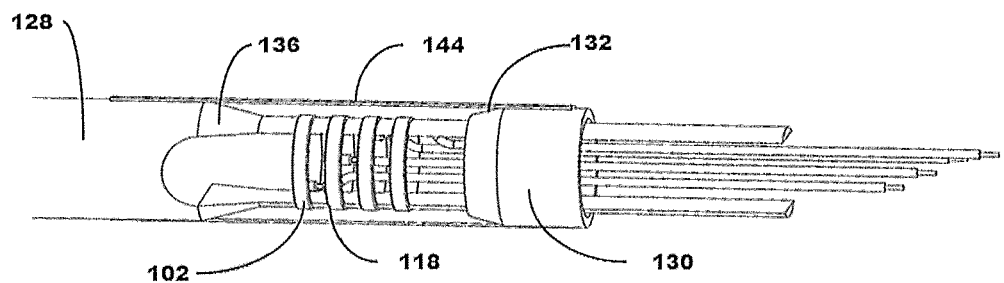
FIG. 8B is a combination schematic view of the assembly shown in FIG. 8A with the shrinkable tube shown in cross-sectional view.

A method for manufacturing a catheter electrode (101) according to the main embodiment of the present invention is described below. This method includes as a first step selecting an alignment tool (126) having an alignment handle (128), a distal shoulder surface (136), two arms or tines (138 and 140) formed by a channel or groove (145) in a longitudinal axis opposite to the alignment handle (128), alignment grooves (142) for the arrangement of the electrode rings (102), and a removable proximal shoulder (130). Then, a series of electrode rings (102) is arranged in the alignment grooves (142) located on the arms or tines (138, 140) of the alignment tool (126) opposed to the alignment handle (128) of the alignment tool (126) (FIG. 7A), wherein conducting wires (110) are positioned usually away from the control surface (134) of the alignment tool (126). To load the electrode rings (102) into the alignment grooves (142), forces F1 and F2 (see FIG. 3B) are applied at the same time to the first arm or tine (138) and to the second arm or tine (140) to compress them or force them to reduce the distance between the tines, thus allowing the arrangement of the electrode rings (102) on the alignment grooves (142). Once the electrode rings (102) are placed on the alignment grooves (142), forces F1 and F2 are released from the arms or tines (138, 140) (see FIGS. 3D to 3H). A proximal shoulder ring (130) having a shoulder surface (132) is then placed at the opposite end of the alignment handle (128) (see FIG. 7B). The conducting wires (110) of electrode ring assemblies (115) are placed through the internal opening (131) of the proximal shoulder ring (130). A heat shrinkable tube (144) slides over the alignment tool (126) covering the outer surfaces (118) of the electrode rings (102) and the distal shoulder surface (136) of the alignment handle (128) (see FIGS. 8A and 8B). Heat shrinkable tube (144) is located adjacent but not necessarily in close contact with the distal shoulder surface (136) of the proximal shoulder ring (130), the outer surfaces (118) of the electrode rings (102) and the distal shoulder surface (136) of the alignment handle (128). It should be noted that the various electrode rings (102) positioned in the tool and the two shoulder surfaces do not need to be of the same diameter or even close in diameter. The only requirement is that the shrinkable tube (144) is sufficiently larger in diameter to slide over all the electrode rings (102), the shoulder surface (132) and the distal shoulder surface (136).

Figure 9:
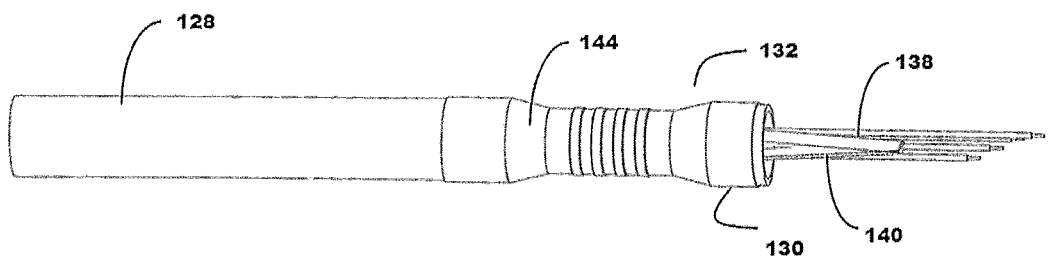
FIG. 9 is another schematic view of an electrode catheter assembly.
Figure 10A:
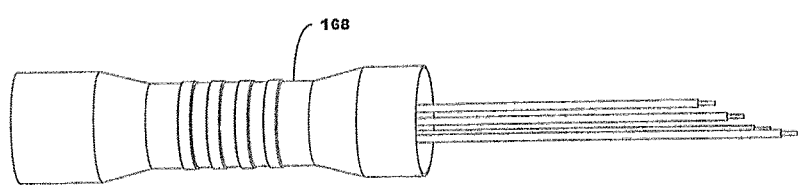
FIG. 10A is a schematic view of an electrode catheter assembly in process, with tool removed.
Figure 10B:
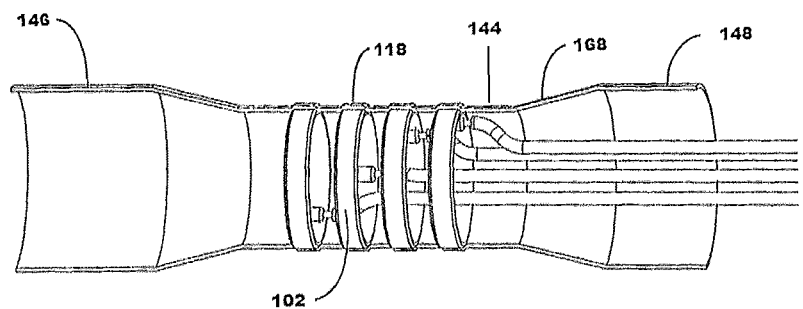
FIG. 10B is a cross-sectional view of the electrode catheter assembly shown in FIG. 10A in combination with the shrinkable tube shown in FIG. 4.
Figure 11A:
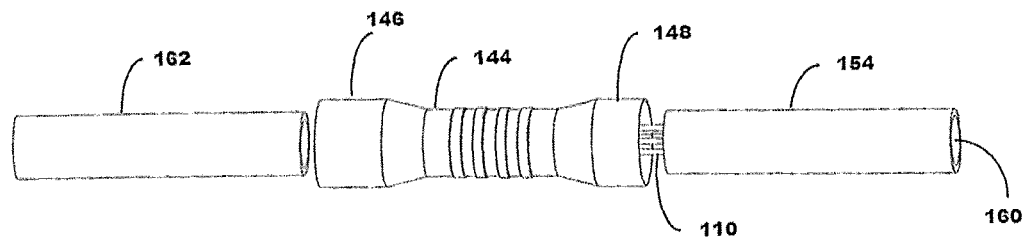
FIG. 11A is a schematic view of an electrode catheter assembly.
Figure 11B:
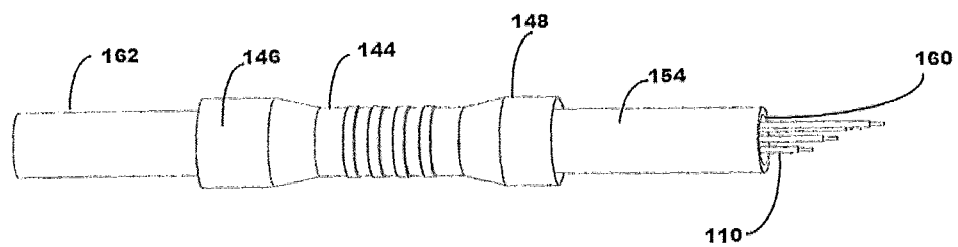
FIG. 11B is another schematic view of an electrode catheter assembly.
Figure 12A:
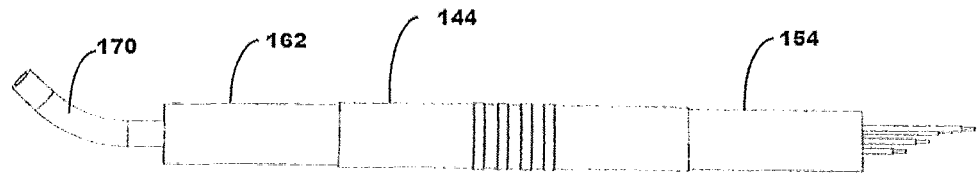
FIG. 12A is a schematic view of a fully heat activated electrode catheter assembly.
Figure 12B:
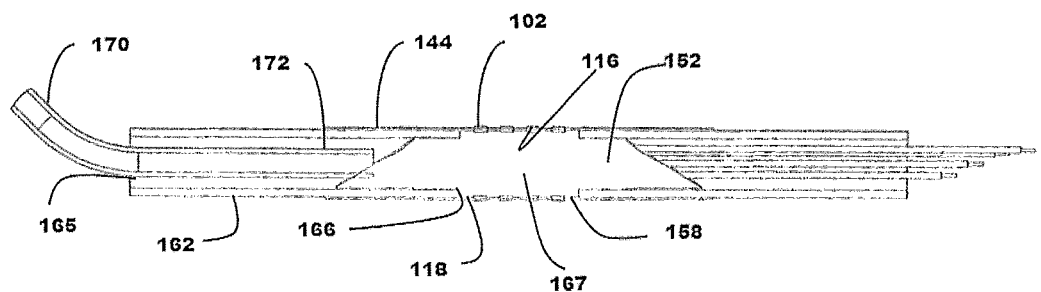
FIG. 12B is a cross-sectional view of the fully heat activated electrode catheter assembly shown in FIG. 12A.
Figure 12C:
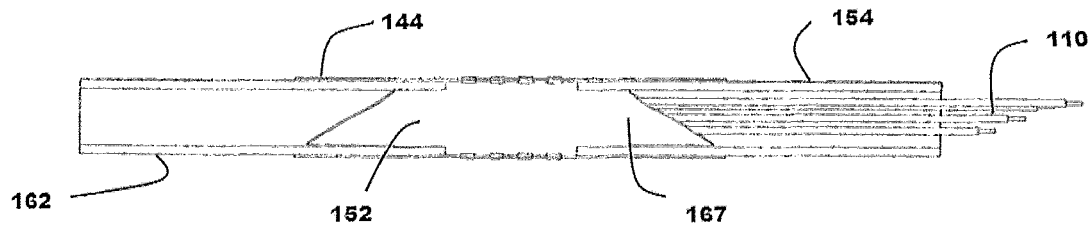
FIG. 12C is a cross-sectional view of an electrode catheter assembly.

The next step is to perform a first heating process to partially shrink the diameter of the shrinkable tube. Depending on the amount of heat applied, typically based on temperature and application time, the shrinkable tube (144) will contract in diameter. For instance, a relatively small amount of applied heat will contract the shrinkable tube diameter a relatively small amount. If an additional heating process is applied later in time, the shrinkable tube (144) will shrink to a smaller diameter. This process of controlled heat application can be repeated until the maximum diameter reduction or shrinkage is attained. Depending on the particular material used, the ultimate reduction in diameter of the shrinkable tube (144) can range from about 95% to about 20% the original diameter. The heat can be applied using an oven or a heated air blower, for example a heat gun, or another device that can apply a controlled amount of heat based on temperature and time of treatment. After the first sufficient heat treatment, the shrinkable tube (144) has made contact and is conformed to the outer surfaces (118) of the electrode rings (102) and at the same time is in contact with the distal shoulder surface (136) and the shoulder surface (132) of the alignment tool (126). Once the heat shrinkable tube (144) has been heat treated and adjusted to the outer surface (118) of the electrode rings (102), and to the distal shoulder surface (136) and to the shoulder surface (132) of the alignment tool (126), then the alignment tool (126) is removed without altering the alignment of the electrode rings (102) when first removing the shoulder proximal ring (130) by sliding it over the conducting wires (110) of the electrode rings (102). Then, once again forces F1 and F2 are applied to the arms or tines (138, 140) for reducing the distance between the tines (138, 140). Once compressed such arms or tines (138, 140), the distance therebetween is reduced to a distance lower than the inner diameter of the proximal shoulder ring (130) to allow the removal of the proximal shoulder ring (130) and alignment handle (128) from the alignment tool (126) without altering the electrode rings (102) in relation to the heat shrinkable tube (144) (see FIG. 9). When the alignment handle (128) is removed, the arms or tines (138, 140) are compressed to avoid any release of the electrode rings (102) in relation to the heat shrinkable tube (144). Once removed the alignment tool (126), it has an assembly (168) (FIG. 10A). FIG. 10B shows an assembly (168) with the shrinkable tube (144) shown in cross sectional view, wherein after applying sufficient heat to partially shrink the shrinkable tube (144), the shrinkable tube (144) is shown in contact with the outer surfaces (118) of the electrode rings (102). The distal end (146) and proximal end (148) of the shrinkable tube (144) have been only partially reduced in diameter, limited in the shrinking process due to the distal shoulder surface (136) and the removable proximal shoulder surface (132) of the removed alignment tool (126). The next step of the method to manufacture an electrode catheter (101) (see FIG. 11A), once the proximal shoulder ring (130) is removed, is to insert the distal catheter tube (162) into the distal end (146) of the shrinkable tube (144) and to insert the proximal catheter tube (154) into the proximal end (148) of the shrinkable tube (144), and at the same time to insert the conducting wires (110) of the electrode ring assembly (115) into the internal lumen (160). This is necessary to ensure that the conducting wires (110) can be eventually bonded to the hub (112) and joined to the connectors (114) later in the manufacturing process of a catheter electrode system as shown in the embodiment of FIG. 1. During the first heating process, the proximal shoulder ring (130) used with the alignment tool (126) provides a shrink limiting surface which is larger in diameter than the outer diameter of the proximal catheter tube (154). Therefore, during the first heating shrink process, the proximal portion of the shrinkable tube (144) will prevent a shrink to a smaller diameter than the diameter of the proximal tube (108) (see FIG. 1). Once the proximal catheter tube (154) has been inserted inside the proximal end (148) of the heat shrinkable tube (144), and the distal catheter tube (162) has been inserted inside the distal end (146) of the heat shrinkable tube (144) (see FIG. 11B), then a second heating process using a controlled heat source to further radially shrink the shrinkable tube (144) until the shrinkable tube (144) is in contact with the outer surface (156) of the proximal catheter tube (154) and the outer surface (164) of the distal catheter tube (162) is applied. The heat shrinkable tube (144) is reduced in diameter sufficiently to be in contact with the distal catheter tube (162) and the proximal catheter tube (154) (see FIG. 12A). Once the inner diameter of the heat shrinkable tube (144) adjusts to the outer diameter of the distal catheter tube (162) and the proximal catheter tube (154), a liquid filler (167) (see FIGS. 12B and 12C) is injected into the inner space (152) of the shrinkable tube (144) sufficiently to make contact with the inner surfaces (116) of all the electrode rings (102), the side surface (166) of the proximal catheter tube (154), the side surface (158) of the distal catheter tube (162). The inner surface (150) of the shrinkable tube (144) is not already in close contact with the outer surfaces (118) of the electrode rings (102), the distal catheter tube (162), or the proximal catheter tube (154). The liquid filler (167) is injected using a syringe, a squeezable bottle or tube, or another injection method. In the embodiments shown in FIGS. 12A and 12B, a cannula (170) is shown to represent the selected injection device, but this should not be limited to so as not to conceive the use of any other injection device. In the embodiment shown in FIGS. 12A and 12B, the tip (172) of the cannula (170) is located within the internal lumen (165) of the distal catheter tube (162). In this position, the liquid filler (167) is injected into the inner space (152) of the shrinkable tube (144). After injection, the liquid filler (167) is hardened to form a bond between the proximal catheter tube (154) and the distal catheter tube (162). The liquid filler (167) in the preferred embodiment is a light curable polyurethane. In other embodiments, it could be, but not limited to, an epoxy resin, a polyurethane adhesive, a silicone adhesive or another adhesive. The material used must be biocompatible after hardening to be used as a component in an electrode catheter assembly (101).

Figure 13A:
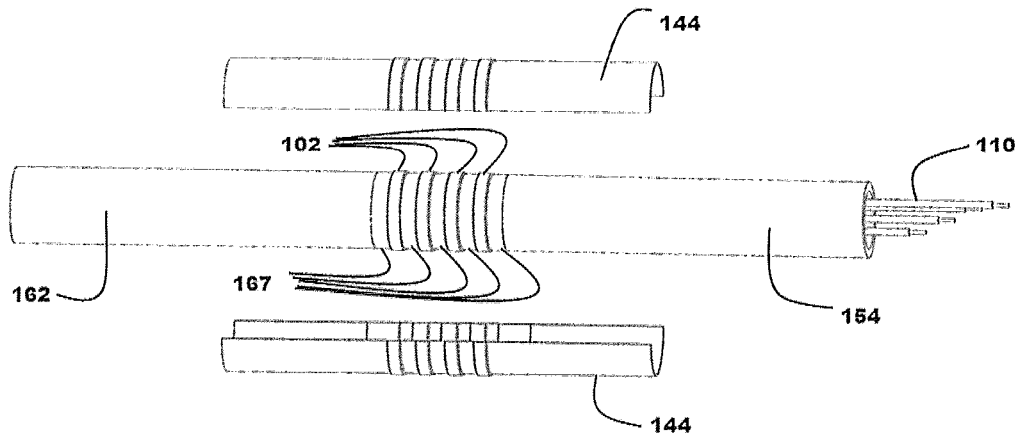
FIG. 13A is a schematic view of an electrode catheter assembly with the shrinkable tubing torn away.
Figure 13B:
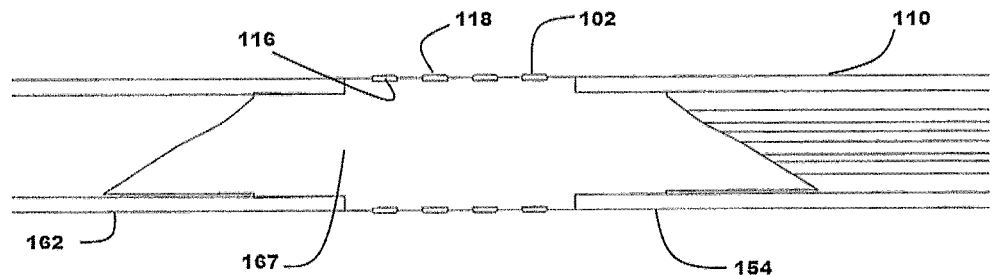
FIG. 13B is a cross-sectional view of the electrode catheter assembly shown in FIG. 13A.

Once the liquid filler (167) is hardened, the shrinkable tube (144) is removed by cutting or tearing (FIGS. 13A and 13B). After removal, an electrode catheter assembly (101) is obtained having the distal catheter tube (162) bonded to the proximal catheter tube (154), and a smooth surface of hardened liquid filler (167) between a series of precisely spaced electrode rings (102) embedded in the hardened liquid filler (167). The outer surfaces (118) of the electrode rings (102) are free of liquid filler (167). This assembly can be further processed to complete the electrode catheter.

In the detailed description of the invention, reference to the figures accompanying this application and which show different embodiments of performing the present invention has been made. It is understandable that other embodiments may be used and that structural changes may be made without separating from the gist and scope of the present invention.

What is claimed is:

1. An alignment tool (126) to be used in a method for the manufacture of an electrode catheter assembly (101), comprising:
   a single-piece alignment handle (128),
   a grooved longitudinal axis, which is opposed to the alignment handle (128), and which is one piece with said alignment handle (128), comprising a channel or groove (145) in the radial direction, wherein the grooved longitudinal axis has alignment grooves (142) and alignment surfaces (143) to precisely allow alignment and separation of electrode rings (102) with each other, wherein the electrode rings (102) are composed of a conductive material, and wherein the inner surfaces of said grooved longitudinal axis are parallel to each other;
   two flexible arms or tines (138, 140) formed by the channel or groove (145), wherein said arms or tines (138, 140) are compressible in radial direction to the grooved longitudinal axis;
   a removable proximal shoulder ring (130), said proximal shoulder ring (130) having a shoulder surface (132) facing toward the electrode rings (102) and a non-conical internal opening (131), wherein the non-conical internal opening allows the shoulder proximal ring (130) to slide on or off the grooved longitudinal axis to arrange a series of the electrode rings (102), wherein the proximal shoulder ring (130) having a shoulder surface (132) is placed at the opposite end of the alignment handle (128) where conducting wires (110) of electrode ring assemblies (115) are placed through the non-conical internal opening (131) of the proximal shoulder ring (130), wherein a heat shrinkable tube (144) slides over the alignment tool (126) covering the outer surfaces (118) of the electrode rings (102) and a distal shoulder surface (136) of the alignment handle (128), wherein the proximal shoulder ring (130) engages on the alignment tool (126) to the alignment handle (128) of the alignment tool (126), and the distal shoulder surface (136) is opposite to the proximal shoulder ring (130) forming a structure in the form of an "hour glass" or "dog bone" when the heat shrinkable tube (144) is heat treated;
   a control surface (134); and
   a distal shoulder surface (136).

2. The alignment tool (126) according to claim 1, wherein the alignment grooves (142) are located at a distance of 1 mm or thereabouts to each other.

3. The alignment tool (126) according to claim 1, wherein the distance between the alignment grooves (142) has a tolerance of tenths of mm or thereabouts.

4. The alignment tool (126) according to claim 1, wherein the alignment handle (128) is made of an elastic material.

5. A method for manufacturing an electrode catheter assembly, comprising the following steps:
   selecting an alignment tool (126) as claimed in claim 1;
   placing and aligning a series of electrode rings (102) on the grooved longitudinal axis of the alignment tool (126) by applying forces F1 and F2 on arms or tines (138, 140) of the alignment tool (126);
   placing a proximal shoulder ring (130) in opposite direction to a distal shoulder surface (136) of the alignment tool (126), wherein the proximal shoulder ring (130) has a shoulder surface (132) and an internal opening (131) to allow that conducting wires (110) pass therethrough;
   sliding a heat shrinkable tube (144) on the outer surface of the electrode rings (102), distal shoulder surface (136) and shoulder surface (132) by releasing the arms or tines (138, 140) from the forces F1 and F2;
   applying a first heat treatment to the heat shrinkable tube (144) to partially reduce its diameter and adjust it to the outer surface (118) of the electrode rings (102), the distal shoulder surface (136) and the shoulder surface (132);
   removing the proximal shoulder ring (130) and the alignment tool (126) by applying forces F1 and F2 to the arms or tines (138, 140);
   inserting a proximal catheter tube (154) into the proximal end (148) of the heat shrinkable tube (144), and a distal catheter tube (162) into the distal end (146) of the heat shrinkable tube (144);
   applying a second heat treatment, which is different to the first heat treatment, to the heat shrinkable tube (144) to reduce its diameter and contact the outer surface of the proximal catheter tube (154) and the outer surface of the distal catheter tube (162);
   injecting sufficient polymer material through the inner space (152) of the heat shrinkable tube (144) for contacting the inner surfaces (116) of the electrode rings (102), the side surface (166) of the proximal catheter tube (154), the side surface (158) of the distal catheter tube (162);
   hardening the polymer material; and
   removing the heat shrinkable tube (144), wherein said heat shrinkable tube (144) is removed by cutting it or tearing it.

6. The method according to claim 5, wherein applying the first heat treatment includes repeatedly applying heat to the shrinkable tube (144) until the maximum diameter reduction or shrinkage is attained.

7. The method according to claim 5, wherein the shrinkable tube (144) is made of a biocompatible material, such as polyurethane, silicone, PEBAX®, nylon, polyvinyl chloride, or polyimide.

8. The method according to claim 5, also wherein the reduction in diameter of the shrinkable tube (144) can range from about 95% to about 20% of the original diameter, depending on the material of the shrinkable tube (144).

9. The method according to claim 7, wherein the shrinkable tube (144) is made of polyurethane.

10. The method according to claim 5, wherein the heat treatments are performed by using an oven or hot air blower.

11. The method according to claim 10, wherein the oven or hot air blower is the type of a heat gun.

12. The method according to claim 5, wherein the electrode rings (102) are aligned to a distance of 1 mm or thereabouts.

13. The method according to claim 12, wherein the distance between the electrode rings (102) has a tolerance of tenths of mm or thereabouts.

14. The alignment tool (126) according to claim 4, wherein the elastic material is selected from plastic or stainless steel or aluminum.

15. The alignment tool (126) according to claim 1, wherein the conductive material is selected from silver or platinum or gold or stainless steel.

\* \* \* \* \*